United States Patent [19]

Cale, Jr. et al.

[11] 4,282,243

[45] Aug. 4, 1981

[54] OPTICAL ISOMERS OF 4-AMINO-N-(1-CYCLOHEXYL-3-PYR- ROLIDINYL)-N-METHYLBENZAMIDE

[75] Inventors: Albert D. Cale, Jr., Mechanicsville; Charles A. Leonard, Richmond, both of Va.

[73] Assignee: A. H. Robins Company, Inc., Richmond, Va.

[21] Appl. No.: 128,693

[22] Filed: Mar. 10, 1980

Related U.S. Application Data

[60] Division of Ser. No. 914,833, Jun. 12, 1978, abandoned, which is a continuation-in-part of Ser. No. 658,989, Feb. 18, 1976, abandoned, which is a continuation-in-part of Ser. No. 518,125, Oct. 25, 1974, abandoned, which is a continuation of Ser. No. 340,417, Mar. 12, 1973, abandoned, which is a continuation-in-part of Ser. No. 240,840, Apr. 30, 1972, abandoned.

[51] Int. Cl.$^3$ .................... C07D 207/14; A61K 31/40
[52] U.S. Cl. ................................ 424/274; 260/326.47
[58] Field of Search ......................................... 424/274

[56] References Cited

U.S. PATENT DOCUMENTS 3,963,745   6/1976   Cale, Jr. ............................... 424/274

Primary Examiner—Mark L. Berch

[57] ABSTRACT

The resolution of racemic 4-amino-N-(1-cyclohexyl-3-pyrrolidinyl)-N-methylbenzamide into the optically active (+) and (−) isomers is disclosed.

2 Claims, No Drawings

OPTICAL ISOMERS OF 4-AMINO-N-(1-CYCLOHEXYL-3-PYRROLIDINYL)-N-METHYLBENZAMIDE

This is a division of application Ser. No. 914,833, filed June 12, 1978, abandoned which is a continuation-in-part of our copending application Ser. No. 658,989 filed Feb. 18, 1976, abandoned which is a continuation-in-part application of copending application Ser. No. 518,125 abandoned filed Oct. 25, 1974, which was a continuation application of Ser. No. 340,417 filed Mar. 12, 1973, now abandoned, which was a continuation-in-part of Ser. No. 240,840 filed Apr. 30, 1972, now abandoned.

The present invention relates to resolving optical isomers of 4-amino-N-(1-cyclohexyl-3-pyrrolidinyl)-N-methylbenzamide of the following formula:

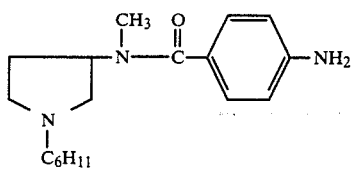

Formula I to the optical isomers thereby obtained, the pharmaceutically acceptable acid addition salts thereof, and to a method for the use of such isomers.

4-Amino-N-(1-cyclohexyl-3-pyrrolidinyl)-N-methylbenzamide possesses valuable therapeutic properties as an anti-emetic and has minimal side effects with a notable absence of cataleptic properties.

The optically active (+) and (−) isomers of the present invention possess useful pharmacological and therapeutic properties as anti-emetics and anti-cataleptics in some ways quite different from those of the corresponding racemic mixture.

It is therefore an object of the present invention to provide (+)-4-amino-N-(1-cyclohexyl-3-pyrrolidinyl)-N-methylbenzamide substantially free from its optical antipode. A further object is to provide a method for the separation of (+)-4-amino-N-(1-cyclohexyl-3-pyrrolidinyl)-N-methylbenzamide from (−)-4-amino-N-(1-cyclohexyl-3-pyrrolidinyl)-N-methylbenzamide. A still further object is to provide pharmaceutical compositions containing as active ingredient the respective (+) and (−) isomers and methods for their use. Additional objects will become apparent from the description which follows and the appended claims.

We have found that the levo-rotary form of 4-amino-N-(1-cyclohexyl-3-pyrrolidinyl)-N-mwethylbenzamide can be readily obtained from the racemic form using (−)-malic acid and that the dextro-rotary form can be readily obtained after separation of (−)-4-amino-N-(1-cyclohexyl-3-pyrrolidinyl)-N-methylbenzamide malate by treating the mother liquors with (+)-malic acid.

The free bases of the levo-rotary and the dextro-rotary forms of 4-amino-N-(1-cyclohexyl-3-pyrrolidinyl)-N-methylbenzamide can be obtained by basifying an aqueous solution of the respective salt with sodium hydroxide and extracting with chloroform. The chloroform solution is then concentrated in vacuo leaving the free base oil which can be crystallized and then recrystallized from isopropyl ether. Alternately, the free base oil may be distilled in a molecular still and then recrystallized from isopropyl ether.

The optically active (+) and (−) isomers of 4-amino-N-(1-cyclohexyl-3-pyrrolidinyl)-N-methylbenzamide in crystalline and substantially pure form and substantially free one from the other are bases which react with pharmaceutically acceptable organic and inorganic acids to produce the corresponding acid addition salts, which have the same activity and are useful for the same purposes as the free bases.

Among the pharmaceutically acceptable acids which can be used to form such salts but not limited thereto are hydrohalic acids such as hydrochloric acid and hydrobromic acid, sulfamic acid, acetic acid, oxalic acid, fumaric acid, maleic acid, benzoic acid, tartaric acid, p-aminobenzoic acid and succinic acid.

The acute toxicities of the ±-racemate, the (+)-isomer and the (−)-isomer were conducted with the fumarate salts and probit analysis (Finney, D. J., Statistical Methods in Biological Assay, Hafner Pub. Co., N. Y., 2nd. Ed., 1964) was employed for the statistical treatment of the mortality data. The data are summarized in Table I.

TABLE I

| Compound | Animal | LD$_{50}$ mg/kg (95% Confidence Limits)[a] | |
|---|---|---|---|
| | | I.P. | P.O. |
| ± racemate | mouse | 90.2 (84.5–96.4) | 181 (166–199) |
| (−)-isomer | mouse | 103.0 (96.0–110.0) | 241 (220–263) |
| (+)-isomer | mouse | 126 (115–139) | 267 (233–313) |
| ± racemate | rat | 111 (103–120) | 305 (272–392) |
| (−)-isomer | rat | 116 (107–130) | 410 (357–500) |
| (+)-isomer | rat | 147 (134–222) | 499 (322–593) |

[a] Expressed as free base

The anti-emetic properties of the fumarate salts were established in dogs using a modification of the anti-apomorphine methods of Chen and Ensor, J. Pharmac. Exp. Ther. 98, 245–250 (1950) and of Leonard et al., J. Pharmac. Exp. Ther. 154, 339–345 (1966) and the ED$_{50}$ was calculated by the method of Goldstein (Biostatistics, An Introductory Text, pg. 156–161, The MacMillan Co., N. Y., 1964). The data are summarized in Table II.

TABLE II

| Compound | Animal | ED$_{50}$ mg/kg, s.c.[a] (95% Confidence Limits) |
|---|---|---|
| ± racemate | dog | 0.25 (0.19–0.31) |
| (−)-isomer | dog | 0.09 (0.05–0.17) |
| (+)-isomer | dog | no significant anti-apormorphine activity |

[a] Expressed as free base

The procedure used for determining cataleptic effects of the fumarate salts was based on that of Tedeschi et al., Arch. Int. Pharmacodyn. Ther. 122, 129–143 (1959). The data are summarized in Table III.

TABLE III

| Compound | Animal | Summary[a] | |
|---|---|---|---|
| | | IP (mg/kg) | PO (mg/kg) |
| ± racemate | rat | NSE to 100[b,c] | NSE to 200 |
| (−)-isomer | rat | ED$_{50}$ > 100[c] | ED$_{50}$ 80 (estimated) |
| (+)-isomer | rat | NSE to 100[c] | NSE to 200 |

[a] Expressed as free base
[b] NSE = no significant cataleptic effect in doses up to indicated amount
[c] Neurotoxic dose level evidenced by seizures in test animals (+)-4-Amino-N-(1-cyclohexyl-3-pyrrolidinyl)-N-methylbenzamide is useful in reducing the cataleptic side effects of known therapeutically effective drugs such as chloropromazine [2-chloro-10-(3-dimethylaminopropyl)phenothiazine] and metoclopramide (N-diethylaminoethyl 2-methoxy-4-amino-5-chlorophenylcarboxamide). The effectiveness is shown in Tables IV and V. In each test the rat was administered a 100% effective cataleptic dose of the test drug followed one hour later by an effective dose of (+)-4-amino-N-(1-cyclohexyl-3-pyrrolidinyl)-N-methylbenzamide.

TABLE IV

Effects on Chlorpromazine-Induced Catalepsy

| Initial Treatment IP | Treatment After One Hour IP | Percent of Rats Cataleptic at: (hours after initial treatment) | | | | | | | |
|---|---|---|---|---|---|---|---|---|---|
| | | 0.5 | 1.0 | 1.5 | 2.0 | 3.0 | 4.0 | 5.0 | 6.0 |
| saline 10 ml/kg | saline 10 ml/kg | 0 | 0 | 0 | 0 | 0 | 0 | 0 | 0 |
| saline 10 ml/kg | (+)-isomer 25 mg/kg | 0 | 0 | 0 | 0 | 0 | 17 | 17 | 0 |
| Chlorpromazine 4 mg/kg | saline 10 mg/kg | 100 | 100 | 100 | 100 | 100 | 100 | 100 | 100 |
| Chlorpromazine 4 mg/kg | (+)-isomer 25 mg/kg | 100 | 100 | 50 | 33 | 33 | 50 | 100 | 67 |

TABLE V

Effects on Metoclopramide-Induced Catalepsy

| Initial Treatment IP | Treatment After One Hour IP | Percent of Rats Cataleptic at: (hours after initial treatment) | | | | | | | | |
|---|---|---|---|---|---|---|---|---|---|---|
| | | 0.5 | 1.0 | 1.5 | 2.0 | 3.0 | 4.0 | 5.0 | 6.0 | 7.0 |
| saline 10 ml/kg | saline 10 mg/kg | 0 | 0 | 0 | 0 | 0 | 0 | 0 | 0 | 0 |
| Metoclopramide 40 mg/kg | saline 10 mg/kg | 100 | 100 | 100 | 100 | 100 | 100 | 100 | 100 | — |
| Metoclopramide 40 mg/kg | (+)-isomer 12.5 mg/kg | 100 | 100 | 100 | 88 | 88 | 100 | 100 | 100 | 100 |
| Metoclopramide 40 mg/kg | (+)-isomer 25 mg/kg | 100 | 100 | 100 | 75 | 38 | 75 | 88 | 88 | — |
| Metoclopramide 40 mg/kg | (+)-isomer 40 mg/kg | 88 | 88 | 25 | 13 | 38 | 38 | 88 | 88 | 88 |
| Metoclopramide 40 mg/kg | (+)-isomer 50 mg/kg | 100 | 100 | 13 | 13 | 25 | 25 | 75 | 88 | 75 |

The invention is illustrated by the following examples without being limited thereto.

EXAMPLE 1

4-Amino-N-(1-cyclohexyl-3-pyrrolidinyl)-N-methylbenzamide cyclohexanesulfamate

4-Nitro-N-(1-cyclohexyl-3-pyrrolidinyl)-N-methylbenzamide was prepared from 15 g. (0.085 mole) of 1-cyclohexyl-3-methylaminopyrrolidine and 15 g. (0.08 mole) p-nitrobenzyl chloride. The 4-nitro-N-(1-cyclohexyl-3-pyrrolidinyl)-N-methylbenzamide was converted to the fumarate salt (8.4 g., 24%) by precipitation with fumaric acid from isopropanol isopropyl ether. The fumarate salt was dissolved in 95% ethanol and hydrogenated at three atmospheres of hydrogen over Raney Nickel for about two hours. The mixture was filtered, the filtrate concentrated and the residue partitioned between dilute sodium hydroxide and chloroform. The chloroform layer was dried and concentrated and the residue treated with hexamic acid in isopropanol-isopropyl ether. Recrystallization from the same solvent gave 5.2 g. (13.5% overall) of the salt melting 196°-199° C.

Analysis: Calculated for $C_{24}H_{40}N_4O_4S$: C, 59.97; H, 8.39; N, 11.66; Found: C, 59.84; H, 8.39; N, 11.55.

EXAMPLE 2

(−)-4-Amino-N-(1-cyclohexyl-3-pyrrolidinyl)-N-methylbenzamide Malate

An ethanol solution containing 20.0 g. (0.067 mole) of 4-amino-N-(1-cyclohexyl-3-pyrrolidinyl)-N-methylbenzamide was treated with 4.94 g. (0.037 mole) of (−)-malic acid and the solution was refrigerated overnight. The crystalline material which separate (m.p. 147°-157° C.) was recrystallized twice from ethanol to give 5.0 g. crystals which melted at 161°-163° C. Rotation $[\alpha]_D^{30}$: −22.65 (water).

Analysis: Calculated for $C_{22}H_{33}N_3O_3$: C, 60.67; H, 7.64; N, 9.65; Found: C, 60.25; H, 7.61; N, 9.64.

EXAMPLE 3

(+)-4-Amino-N-(1-cyclohexyl-3-pyrrolidinyl)-N-methylbenzamide Malate

The mother liquor and filtrates from Example 2 were combined and concentrated. The residue was partitioned between chloroform and dilute sodium hydroxide. The chloroform was concentrated and the residue in ethanol solution was treated with 2 g. of (−)-malic acid and placed in the refrigerator overnight. The resulting solid was filtered and discarded. The filtrate was concentrated and partitioned between chloroform and dilute sodium hydroxide. The chloroform was concentrated and the residue treated with 2 g. of (+)-malic acid in ethanol. The resulting crystals were recrystallized from ethanol. Yield 2.2 g., m.p. 161°-163° C.

Rotation $[\alpha]_D^{30}$: +24.81 (water).

Analysis: Calculated for $C_{22}H_{33}N_3O_6$: C, 60.67; H, 7.64; N, 9.65; Found: C, 60.41; H, 7.66; N. 9.55.

EXAMPLE 4

(−)-4-Amino-N-(1-cyclohexyl-3-pyrrolidinyl)-N-methylbenzamide Fumarate

An aqueous solution containing 3.9 g. (0.0094 mole) of (−)-4-amino-N-(1-cyclohexyl-3-pyrrolidinyl)-N-methylbenzamide malate was made basic with sodium hydroxide and the basic solution was extracted with chloroform, the chloroform solution was dried over sodium sulfate and concentrated in vacuo. The thick oily residue is the free base, (−)-4-amino-N-(1-cyclohexyl-3-pyrrolidinyl)-N-methylbenzamide fumarate. The residue was dissolved in ethanol, 1.2 g. (0.01 mole) of fumaric acid added and the solution refrigerated. The fumarate salt which separated weighed 3.3 g. and melted at 205°–207° C.

Rotation $[\alpha]_D^{30}$: −13.89 (methanol).

Analysis: Calculated for $C_{22}H_{31}N_8O_5$: C, 63.29; H, 7.48; N, 10.06; Found: C, 63.12; H, 7.47; N, 10.11.

EXAMPLE 5

(+)-4-Amino-N-(1-cyclohexyl-3-pyrrolidinyl)-N-methylbenzamide Fumarate

An aqueous solution of 2.2 g. (0.005 mole) of (+)-4-amino-N-(1-cyclohexyl-3-pyrrolidinyl)-N-methylbenzamide malate was made basic using sodium hydroxide and the basic solution was extracted with chloroform. The dried chloroform solution was concentrated in vacuo. The thick oily residue is the free base, (+)-4-amino-N-(1-cyclohexyl-3-pyrrolidinyl)-N-methylbenzamide. The residue was treated with a solution of 0.6 g. (0.005 mole) The residue was treated with a solution of 0.6 g. (0.005 mole) of fumaric acid in ethanol-methanol. The fumarate salt which separated weighed 1.6 g. and melted at 204°–206° C.

Rotation $[\alpha]_D^{30}$: +12.72 (methanol).

Analysis: Calculated for $C_{22}H_{31}N_3O_5$: C, 63.29; H, 7.48; N, 10.06; Found: C, 63.71; H, 7.39; N, 9.85.

EXAMPLE 6

(−)-4-Amino-N-(1-cyclohexyl-3-pyrrolidinyl)-N-methylbenzamide

Three grams (0.007 mole) of (−)-4-amino-N-(1-cyclohexyl-3-pyrrolidinyl)-N-methylbenzamide fumarate was partitioned between chloroform and dilute sodium hydroxide. The chloroform solution was dried with anhydrous sodium sulfate and concentrated in vacuo on a steam bath. The residue was distilled on a molecular still at 0.1 mm pressure and 190° C. The distillate was crystallized from isopropyl ether. Yield 1.5, m.p. 106°–108° C.

Rotation $[\alpha]_D^{25}$: −46.81 (chloroform).

Analysis: Calculated for $C_{18}H_{27}N_3O$: C, 71.72; H, 9.03; N, 13.94; Found: C, 71.97; H, 9.08; N, 13.85.

EXAMPLE 7

(+)-4-Amino-N-(1-cyclohexyl-3-pyrrolidinyl)-N-methylbenzamide

Two grams (0.005 mole) of (+)-4-amino-N-(1-cyclohexyl-3-pyrrolidinyl)-N-methylbenzamide fumarate was partitioned between chloroform and dilute sodium hydroxide. The chloroform solution was dried with anhydrous sodium sulfate and concentrated. On standing overnight the oil crystallized and was recrystallized from isopropyl ether. Yield 1.3 g., m.p. 106.5°–108° C.

Rotation $[\alpha]_D^{25}$: +48.55 (chloroform).

Analysis: Calculated for $C_{18}H_{27}N_3O$: C, 71.62; H, 9.03; N, 13.94; Found: C, 71.77; H, 9.08; N, 13.96.

The pharmaceutical compositions of this invention comprise the anti-emetic (−)-isomer and the anti-cataleptic (+)-isomer of Formula I as the active ingredient in an amount to provide said activity. The compositions contain 1.0 mg. to 100 mg. of the respective isomer per unit dose. Preferably, the compositions contain from about 5 mg. to 100 mg. of the active ingredient, advantageously from about 5 mg. to about 50 mg. per unit dose.

The pharmaceutical carrier employed in the composition can be either solid or liquid. Exemplary of solid carriers are lactose, magnesium stearate, terra alba, sucrose, talc, stearic acid, gelatin, agar, pectin or acacia. Exemplary of liquid carriers are vegetable oils and water. Similarly, the carrier or diluent may include a sustained release material such as glyceryl monostearate or glyceryl distearate alone or with a wax.

A wide variety of pharmaceutical forms can be employed. Thus, if a solid carrier is used the composition can be tableted or prepared as a powder, a troche, a lozenge or a suppository. Gelatin capsules containing the medicament can also be prepared. If a liquid carrier is used, the composition can be in the form of a soft gelatin capsule, a liquid suspension or a syrup. Parenteral dosage forms are obtained by dissolving a water-soluble salt of the active ingredient in water or saline solution in a concentration such that 1 cc. of the solution contains from 1.0 mg. to 25 mg. of active ingredient. The solution can then be filled into single or multiple dose ampules.

The method in accordance with this invention comprises administering internally to warm blooded animals including human beings (+)-4-amino-N-(1-cyclohexyl-3-pyrrolidinyl)-N-methylbenzamide to control catalepsy and (−)-4-amino-N-(1-cyclohexyl-3-pyrrolidinyl)-N-methylbenzamide to control emesis or a nontoxic organic or inorganic acid addition salt thereof, preferably with a nontoxic pharmaceutical carrier such as described above. The active isomer is administered orally or parenterally in repeated doses until satisfactory response is obtained. The daily dosage is from about 10 mg. to about 300 mg. of active medicament, advantageously from about 5 mg. to 50 mg.

Various modifications and equivalents will be apparent to one skilled in the art, and may be made in the compounds, compositions of the present invention without departing from the spirit or scope thereof, and it is to be understood that the invention is to be limited only by the scope of the appended claims.

What is claimed is:

1. A method for reducing the effects of drug-induced catalepsy in warm-blooded animals which comprises administering internally to animals in need thereof an effective amount of (+)-4-amino-N-(1-cyclohexyl-3-pyrrolidinyl)-N-methyl benzamide fumarate in the presence of a pharmaceutical carrier thereof.

2. A method for reducing the effects of drug-induced catalepsy in warm-blooded animals which comprises administering internally to animals in need thereof an effective amount of (+)-4-amino-N-(1-cyclohexyl-3-pyrrolidinyl)-N-methyl benzamide malate in the presence of a pharmaceutical carrier therefor.

* * * * *